United States Patent [19]

Hoegerle et al.

[11] Patent Number: 4,560,402
[45] Date of Patent: Dec. 24, 1985

[54] 2,4-DIAMO-5-(ALKYLSULFINYL) OR ALKYLSULPHONYL)-6-HALOPYRIMIDINES

[75] Inventors: Karl Hoegerle, Basel; Hans Tobler, Allschwil, both of Switzerland

[73] Assignee: Ciba Geigy Corporation, Ardsley, N.Y.

[21] Appl. No.: 174,983

[22] Filed: Aug. 4, 1980

[30] Foreign Application Priority Data

Aug. 15, 1979 [CH] Switzerland ............... 7478/79
Aug. 15, 1979 [CH] Switzerland ............... 7479/79

[51] Int. Cl.$^4$ ............... C07D 239/24; A01N 43/54
[52] U.S. Cl. ............... 71/092; 544/298; 544/322
[58] Field of Search ............... 544/320, 298; 71/92

[56] References Cited

U.S. PATENT DOCUMENTS 3,124,447  3/1964  Wineman et al. ............ 71/103
3,968,214  7/1976  Claverie et al. ............ 544/298
4,014,677  3/1977  Fischer ............ 544/320
4,082,535  4/1978  Hoegerle et al. ............ 544/326
4,412,074 10/1983  Hoegerle et al. ............ 544/298

Primary Examiner—Nicholas S. Rizzo

Attorney, Agent, or Firm—Edward McC. Roberts; Frederick H. Rabin

[57] ABSTRACT

The invention relates to novel 2,4-diamino-5-alkylsulfinyl- or -alkylsulfonyl-6-halopyrimidines of the formula

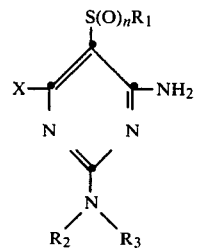

wherein n is 1 or 2, $R_1$ is $C_1$–$C_4$alkyl, each of $R_2$ and $R_3$ is hydrogen, $C_1$–$C_6$alkyl or $C_3$–$C_6$cycloalkyl and X is chlorine, bromine or fluorine. These compounds have selective herbicidal action and inhibit plant growth. They are obtained by amination of halogen-substituted or hydroxyl-substituted amino-5-alkylsulfinyl- and -sulfonylpyrimidines. The invention also relates to the production of 5-sulfinylpyrimidine intermediates.

9 Claims, No Drawings

2,4-DIAMO-5-(ALKYLSULFINYL) OR ALKYLSULPHONYL)-6-HALOPYRIMIDINES

The present invention relates to novel pyrimidines, processes for their production, herbicidal and plant growth-regulating compositions which contain these novel compounds, and to methods of selectively controlling weeds in crops of useful plants or of inhibiting plant growth which comprise the use of the novel compounds. The invention further relates to 5-sulfinylpyrimidines which are used as intermediates for obtaining the pyrimidines of this invention, and to processes for their production.

The pyrimidines of the present invention have the formula I

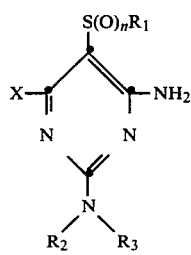
(I)

wherein n is 1 or 2, $R_1$ is $C_1$-$C_4$alkyl, $R_2$ and $R_3$ are hydrogen, $C_1$-$C_6$alkyl or $C_3$-$C_6$cycloalkyl, and X is chlorine, bromine or fluorine.

The term "alkyl" comprises all straight-chain and branched groups which come under its definition.

The pyrimidines of the formula I are novel compounds. They possess in general pronounced selective herbicidal properties and are especially useful for controlling weeds in crops of useful plants, particularly in crops of maize as well as soybeans, cotton, cereals such as barley and oats, and also of sugar beet.

The compounds also act as total herbicides when employed in a sufficiently high rate of application. Application can be both pre- and postemergence and the rates of application can vary within wide limits, e.g. from 0.1 to 10 kg of active ingredient per hectare, with the preferred range being from 0.5 to 5 kg/ha. With some compounds, however, good selective herbicidal activity has been observed at a rate of application of only 0.25 kg/ha.

The compounds of the formula I also have plant growth-regulating action, for example growth inhibition in cereals. This inhibition affects only vegetative growth, resulting in cereals with shorter yet stronger stalks which are not so easily lodged by gales or heavy rain. The generative growth is retained, and the more advantageous conditions even lead to increases in yield.

A very large number of pyrimidines with herbicidal action or which otherwise influence plant physiology are known, e.g. from J. prakt. Chemie 115, p. 292 (1927), German Offenlegungsschrift No. 2 006 145 and 2 356 644, or more recently, from European patent publication No. 681.

The pyrimidines of the present invention are obtained in a manner which is known per se. A first method consists in reacting a 2,4,6-trihalo-4-alkylsulfinylpyrimidine or -alkylsulfonylpyrimidine of the formula II

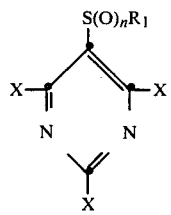
(II)

wherein n, $R_1$ and X are as defined for formula I, in a solvent which is inert to the reactants and in the presence of a base which acts as acid acceptor, with a substantially equimolar amount of the amine of the formula III

(III)

wherein $R_2$ and $R_3$ are as defined for formula I.

In addition to undesired 4-amino-2,6-dihalo-5-alkylsulfinylpyrimidine or -alkylsulfonylpyrimidine, the above reaction affords 2-amino-4,6-dihalo-5-alkylsulfinylpyrimidine or -alkylsulfonylpyrimidine of the formula IV

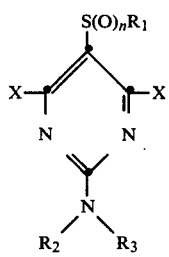
(IV)

wherein n, $R_1$, $R_2$, $R_3$ and X have the given meanings. Separation of the two isomers is effected by column chromatography or fractional crystallisation. The 2-amino compounds are more readily water-soluble than the 4-amino isomers. The separation can be performed such that the isomers are obtained in quantitative yield.

The first process for the production of the pyrimidines comprises reacting the 2-amino-4,6-dihalo-5-alkylsulfinylpyrimidine or -alkylsulfonylpyrimidine of the formula IV above, in an inert solvent, with twice the molar of amount of ammonia or of an amine. These reactions are carried out in the temperature range from 0° C. to about 150° C., i.e. up to the boiling point of the solvent, or under pressure in a closed vessel.

Solvents which may conveniently be employed are those which are inert to the reactants, e.g. water, methylene chloride, chloroform, dioxan, tetrahydrofurane, dimethyl formamide, methanol, ethanol, isopropanol, methyl ethyl ketone, diethyl ketone, toluene etc. Mixtures of these solvents with one another or with water can also be used.

The 5-alkylsulfonyl-2,4,6-trihalopyrimidines of the formula II and methods of obtaining them are described e.g. in German Offenlegungsschrift No. 2 819 837 or in French Pat. No. 2 390 436. They are obtained by reacting barbituric acid, in the presence of a base, with an alkylsulfonyl halide to give alkylsulfonylbarbituric acid, which is then treated, in a solvent, with N,N-dimethylaniline and phosphoroxy chloride.

The 5-alkylsulfinyl-2,4,6-trihalopyrimidines of the formula II are obtained by oxidation of 2-alkylthio-2,4,6-trihalopyrimidines [described in J. of Medicinal Chemistry 18, p. 553 (1975)] with a relatively mild oxidising agent, e.g. peracetic acid, 3-chlorobenzoic acid, perbenzoic acid, hydrogen peroxide, sodium periodate, perlauric acid, iodobenzodichloride, N-chlorosuccinimide, N-bromosuccinimide. Depending on the oxidising agent employed, suitable solvents are methylene chloride, chloroform, acetic acid, water etc. The oxidation is carried out in the temperature range from −50° to +50° C. Similar oxidation reactions are described e.g. in Tetrahedron Letters 1973, p. 2365, cf. also "Organic Compounds of Bivalent Sulfur", Vol. 2, p. 64 (Chemical Publishing Co. New York).

A further method of obtaining the pyrimidine compounds of the formula I comprises reacting a 2-amino-4,6-dihydroxypyrimidine of the formula V

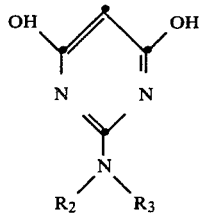
(V)

wherein $R_2$ and $R_3$ have the given meanings, in alkaline medium, with an alkylsulfonyl or alkylsulfinyl halide of the formula VI

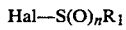

Hal—$S(O)_n R_1$ (VI)

wherein Hal is chlorine or bromine and n and $R_1$ have the given meanings. The 2-amino-4,6-dihydroxy-5-alkylsulfinylpyrimidine or -alkylsulfonylpyrimidine obtained is precipitated by acidifying the reaction mixture and isolated, and by subsequent reaction with a strong halogenating agent such as phosphoroxy chloride, phosphoroxy bromide, sulfuryl chloride or sulfuryl bromide, optionally in the presence of a basic catalyst, preferably N,N-dimethylaniline, chlorinated to give the 2-amino-4,6-dihalo-5-alkylsulfinylpyrimidine or -alkylsulfonylpyrimidine of the formula IV above, which is then reacted with twice the molar amount of ammonia or of an amine to give the pyrimidines of the formula I.

The reaction conditions and solvents employed in this method are substantially the same as for the first preparatory method. The starting materials of the formula V are known and their production is described e.g. in Journal of the Chemical Society, 1967, p. 2146, and Chemische Berichte 96, p. 2786 (1963).

Finally, another method of obtaining the pyrimidines of the formula I comprises reacting a 2,4-diamino-6-hydroxypyrimidine of the formula VII

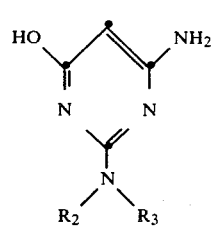
(VII)

wherein $R_2$ and $R_3$ have the given meanings, in alkaline medium, with an alkylsulfinyl or alkylsulfonyl halide of the formula VI above, to give a 2,4-diamino-5-alkylsulfinyl- or -alkylsulfonyl-6-hydroxypyrimidine of the formula VIII

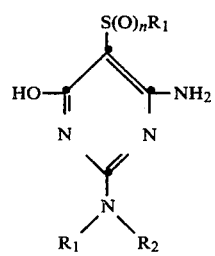
(VIII)

wherein n, $R_1$, $R_2$ and $R_3$ have the given meanings, and precipitating this product by acidifying the reaction mixture, and then isolating it.

The pyrimidines of the formula I are then obtained by reacting the 2,4-diamino-5-alkylsulfinyl- or -alkylsulfonyl-6-hydroxypyrimidine of the formula VIII above with a strong halogenating agent such as phosphoroxy chloride, phosphoroxy bromide, sulfuryl chloride or sulfuryl bromide.

The above reactions are carried out under similar conditions to, and in the same solvents as, the first preparatory method. The starting materials of the formula VII are known and are described e.g. in Journal of Organic Chemistry, Vol. 28, p. 2672, (1963).

The pyrimidines of the formula I are stable compounds which are soluble in customary organic solvents such as alcohols, ethers, ketones, dimethyl formamide, dimethylsulfoxide etc. They are relatively non-toxic, and no special precautionary measures are required for handling them.

The compositions of the present invention are obtained in known manner by intimately mixing and grinding active ingredients of the general formula I with suitable carriers and/or adjuvants, with or without the addition of anti-foam agents, wetting agents, dispersants and/or solvents which are inert to the active ingredients. The active ingredients can be processed to the following formulations:

solid formulations: dust, tracking powders, granules (coated granules, impregnated granules and homogeneous granules),
active ingredient concentrates which are dispersible in water: wettable powders, pastes, emulsions, emulsifiable concentrates:
liquid formulations: solutions.

The concentrations of active ingredient in the compositions of this invention are between 1 and 80 percent by weight. As circumstances may require, the active ingredients can also be applied in low concentrations of about 0.05 to 1 percent by weight.

The compositions of the present invention can be mixed with other biocidal compounds or compositions. Thus in addition to containing the compounds of the general formula I, the compositions of the invention can also contain e.g. insecticides, fungicides, bactericides, fungistatic agents, bacteriostatic agents, nematocides or further herbicides, in order to broaden the activity spectrum.

The following Examples illustrate the invention in more detail.

They describe the production of the pyrimidines of the formula I and of the 5-sulfinylpyrimidine intermediates, and also the preparation of ready-for-use formulations and concentrates which contain the active ingredients. Finally, experimental methods of determining the herbicidal and plant growth-regulating action of the novel compounds are described. Throughout, pressures are in millibars and parts and percentages are by weight.

EXAMPLE 1

2,4-Diamino-5-methylsulfonyl-6-chloropyrimidine

Dry ammonia is introduced at 5°–10° C. into a solution of 26.2 g (0.1 mole) of 5-methylsulfonyl-2,4,6-trichloropyrimidine in 250 ml of methylene chloride, and the reaction mixture is stirred for 2 hours at this temperature and then for 16 hours at room temperature. The suspension is filtered and the filter cake is washed with methylene chloride and with water. The crystals are dried and recrystallised from 200 ml of boiling methyl cellosolve, affording 12 g of 4,6-diamino-5-methylsulfonyl-2-chloropyrimidine with a melting point of 280°–281° C. The methyl cellosolve filtrate is diluted with the same volume of ethanol and the precipitated crystals are filtered with suction after 2 days, yielding 2.5 g of 2,4-diamino-5-methylsulfonyl-6-chloropyrimidine with a melting point of 256°–258° C.

The starting 5-methylsulfonyl-2,4,6-trichloropyrimidine is obtained as follows:

(a) A solution of 25 g (0.143 mole) of 96% methanesulfonyl anhydride in 25 ml of acetone is added dropwise at room temperature to a solution of 11.9 g (0.09 mole) of barbituric acid in 200 ml of water and 18 ml of N sodium hydroxide. The pH is kept at 11.5–12 by addition of 30 ml of 5N sodium hydroxide. The reaction is complete (constant pH) after stirring the reaction mixture for 4 hours at room temperature. The suspension is acidified (pH 1) with 20 ml of conc. hydrochloric acid and the precipitate is collected by filtration, affording 17.7 g (86% of theory) of the sodium salt of 5-methylsulfonylbarbituric acid.

(b) 12.5 ml (0.1 mole) of N,N-dimethylaniline are slowly added at room temperature to 100 ml of phosphoroxy chloride. To this solution are added 22.8 g (0.1 mole) of the barbituric acid (sodium salt or a corresponding amount of the free acid) obtained in (a) above. The reaction mixture is heated, whereupon hydrogen chloride slowly begins to evolve at about 55° C. The suspension is refluxed for 15 to 20 hours, then the turbid solution is poured into water at 25°–28° C. and the mixture is stirred for 20 minutes. The precipitate (17.6 g) is dried in air and then taken up in methylene chloride. The solution is treated with carbon and sodium sulfate, then filtered clear, and the filtrate is evaporated to dryness, affording 17.3 g of solid. This solid is dissolved in 100 ml of toluene and the solution is treated with activated carbon, filtered clear, cooled, and allowed to crystallise out. Finally, about 15.8 g (~60.4% of theory) of 5-methylsulfonyl-2,4,6-trichloropyrimidine are obtained from several crystal fractions. The main fraction has a melting point of 146°–147° C.

EXAMPLE 2

2,4-Diamino-5-methylsulfonyl-6-chloropyrimidine 130 ml of 25% ammonia are added dropwise in the course of 30 minutes to a suspension of 155.4 g (0.64 mole) of 2-amino-4,6-dichloro-5-methylsulfonylpyrimidine in 750 ml of methyl cellosolve. The suspension is heated in the course of 5 hours to 60° C., stirred overnight at room temperature and filtered, affording 112.5 g of the above compound with a melting point of 250°–252° C. Recrystallisation from methyl cellosolve brings the melting point up to 259°–261° C.

The starting material is obtained is follows:

(a) 2-Amino-2,6-dihydroxy-5-methylsulfonylpyrimidine

While cooling with ice, 296 g (2.58 mole) of 98% methanesulfonyl chloride are added dropwise at 5°–10° C. and in the course of 4 hours at pH 11.5–12 to a solution of 218 g (1.71 moles) of 2-amino-4,6-dihydroxypyrimidine in 2300 ml of water and 170 ml of 30% sodium hydroxide. The pH of 11.5–12 is kept by the simultaneous dropwise addition of about 700 ml of 5N sodium hydroxide. The reaction mixture is stirred for 1 hour in an ice bath and then filtered, affording 319.9 g (81.8% of theory) of the sodium salt of the above compound, from which the free acid can be isolated by reaction with hydrochloric acid.

(b) 2-Amino-4,6-dichloro-5-methylsulfonylpyrimidine 187 g (0.91 mole) of 2-amino-4,6-dihydroxy-5-methylsulfonylpyrimidine are sprinkled into a solution of 116 ml (0.91 mole) of dimethylaniline in 1500 ml of phosphoroxy chloride. The suspension is slowly heated to reflux and kept at this temperature until the evolution of hydrochloric acid has ceased. The phosphoroxy chloride is stripped off in a rotary evaporator and the honey-like residue is poured in small amounts into 1000 ml of water, while keeping the temperature at 20°–25° C. by addition of ice. The solution is clarified by removing brown sludge and the pH is adjusted from about 0.5 to 4.5 with sodium acetate. The separated dimethylaniline is removed by two extractions with ether and the clear aqueous phase is warmed to 40°–45° C. and kept for 1 hour at this temperature. The suspension is stirred overnight and filtered at 10° C., affording 155.4 g of the above product which melts at 275° C. with decomposition. A further 16.8 g of the same compound crystallise from the mother liquor after prolonged standing.

EXAMPLE 3

2-Methylamino-4-amino-5-methylsulfonyl-6-chloropyrimidine

While cooling with ice, 18 ml (0.25 mole) of 25% ammonia solution are added dropwise in the course of about 1 hour to a solution of 26.15 g (0.1 mole) of 5-methylsulfonyl-2,4,6-trichloropyrimidine in 300 ml of methylene chloride. The suspension is stirred overnight at 0°–5° C. and, after addition of the same volume of water, well stirred and filtered over a suction filter. The filter cake (18 g) is dissolved hot in 80 ml of dimethyl formamide and 170 ml of methanol are added to the solution, whereupon 6.2 g of pure 4-amino-5-methylsulfonyl-2,6-dichloropyrimidine crystallise out (analysis by thin-layer chromatography). This product is dissolved in 150 ml of acetonitrile and to the solution is added a solution of 3.9 g of 41% aqueous methylamine in 50 ml of acetonitrile. The suspension is stirred overnight at 40° C., then evaporated to dryness in a rotary evaporator, and the residue is stirred with water.

The bulk of the undesired 4,6-isomer is removed from the water-insoluble constituent by crystallisation from acetic acid/water (1:2). The mother liquor is evaporated to dryness and the residue is chromatographed over 200 g of silica gel with chloroform/ethyl acetate (1:1) as eluant. According to IR and C-NMR spectral analysis, the second, more slowly developing zone is the desired 2-methylamino-4-amino-5-methylsulfonyl-6-chloropyrimidine with a melting point of 212°–214° C.

EXAMPLE 4

2,4-Diamino-5-methylsulfinyl-6-chloropyrimidine

A mixture of 20 g (0.08 mole) of 2,4,6-trichloro-5-methylsulfinylpyrimidine, 12 g (0.7 mole) of gaseous ammonia and 100 ml of isopropanol is reacted in an autoclave for 5 hours at 100° C. The reaction mixture is concentrated and the residue is washed with water. The melting point of the crude product is 205°–207° C. Recrystallisation from methyl cellosolve yields 6.3 g of crystals with a melting point of 221°–223° C. and 4.3 g of crystals with a melting point of 218°–220° C., giving a total yield of 10.6 g (64% of theory). According to 13 C-NMR spectral analysis, the product is the desired 2,4-diamino-5-methylsulfinyl-6-chloropyrimidine.

The starting 2,4,6-trichloro-5-methylsulfinylpyrimidine is obtained as follows:

(a) 156 g (0.81 mole) of 90% 3-perchlorobenzoic acid in 1.5 liters of methylene chloride are added dropwise at −5° C. to a solution of 186.8 g (0.81 mole) of 2,4,6-trichloro-5-methylthiopyrimidine in 2 liters of methylene chloride. The reaction mixture is stirred for 15 hours at room temperature and then filtered. The filtrate is washed twice with 1N NaOH and once with water, dried over $Na_2SO_4$, concentrated, and the residue is crystallised from ethyl acetate/petroleum ether, affording 147.3 g (74% of theory) of the title compound with a melting point of 126°–128° C.

The following pyrimidines of the formula I are obtained in analogous manner:

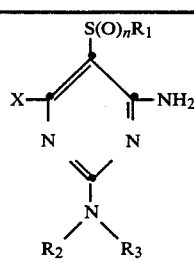

| Compound | X | $S(O)_nR_1$ | $NR_2R_3$ | Physical data (°C.) |
|---|---|---|---|---|
| 1 | Cl | $SO_2CH_3$ | $NH_2$ | m.p. 256–8° |
| 2 | Cl | $SO_2CH_3$ | $NHCH_3$ | m.p. 212–4° |
| 3 | Cl | $SOCH_3$ | $NH_2$ | m.p. 221–3° |
| 4 | Cl | $SO_2CH_3$ | $N(CH_3)_2$ | m.p. 137–8° |
| 5 | Cl | $SO_2CH_3$ | $NHC_3H_7iso$ | m.p. 122–3° |
| 6 | Cl | $SOCH_3$ | $NHCH_3$ | m.p. 215° (decompos.) |
| 8 | Cl | $SOCH_3$ | $N(CH_3)_2$ | m.p. 122–4° |
| 9 | Cl | $SOCH_3$ | $NHC_2H_5$ | m.p. 161–2° |
| 10 | Br | $SO_2C_2H_5$ | $NH_2$ | |
| 11 | Cl | $SO_2C_2H_5$ | $N(C_2H_5)_2$ | |

-continued

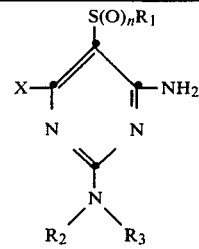

| Compound | X | $S(O)_nR_1$ | $NR_2R_3$ | Physical data (°C.) |
|---|---|---|---|---|
| 12 | Br | $SO_2CH_3$ | $N(CH_3)_2$ | |
| 13 | F | $SO_2CH_3$ | $NH_2$ | m.p. 215–6° |
| 14 | Cl | $SO_2C_4H_9n$ | $NH_2$ | m.p. 220–2° |
| 15 | Cl | $SOCH_3$ | $NHC_3H_7iso$ | m.p. 133–5° |
| 16 | Cl | $SOCH_3$ | $NHC_3H_7n$ | m.p. 150–3° |
| 17 | Cl | $SOCH_3$ | NH-cyclopropyl | m.p. 155–6° |
| 18 | Cl | $SOCH_3$ | $NHC_6H_{13}n$ | m.p. 100–02° |
| 19 | Cl | $SOCH_3$ | $NHC_4H_9t$ | m.p. 156–60° |
| 20 | F | $SOCH_3$ | $NH_2$ | m.p. 221–2° |

The following intermediates of formulae II, IV and VIII are also obtained:

| $S(O)_nR_1$ | A | B | C | Physical data (°C.) |
|---|---|---|---|---|
| $SOCH_3$ | Cl | Cl | Cl | m.p. 126–8° |
| $SO_2CH_3$ | $NH_2$ | OH | OH | m.p. >300° decompos. |
| $SO_2CH_3$ | $NH_2$ | Cl | Cl | m.p. 275° decompos. |
| $SO_2C_2H_5$ | Cl | Cl | Cl | m.p. 135–6° |
| $SO_2C_4H_9n$ | Cl | Cl | Cl | m.p. 71–2° |

EXAMPLE 5

Preparation of ready-for-use formulations and active ingredient concentrates

Wettable Powder

The following constituents are used to formulate (a) a 70% and (b) a 10% wettable powder:

(a)
- 70 parts of a pyrimidine of the formula I,
- 5 parts of sodium dibutylnaphthylsulfonate,
- 3 parts of naphthalenesulfonic acid/phenolsulfonic acid/formaldehyde condensate (3:2:1),
- 10 parts of kaolin,
- 12 parts of Champagne chalk;

(b)
- 10 parts of active ingredient,
- 3 parts of a mixture of the sodium salts of saturated fatty alcohol sulfates,
- 5 parts of naphthalenesulfonic acid/formaldehyde condensate,
- 83 parts of kaolin.

The pyrimidine is applied to the corresponding carriers (kaolin and chalk) and then these are mixed and ground with the other ingredients to yield wettable powders of excellent wettability and suspension power. By diluting these wettable powders with water it is possible to obtain suspensions containing 0.1 to 80% of active ingredient. These suspensions are suitable for controlling weeds in crops of cultivated plants.

Paste

The following substances are used to formulate a 45% paste:
45 parts of a pyrimidine of the formula I,
5 parts of sodium aluminum silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The pyrimidine is intimately mixed with the additives in appropriate devices and ground. By diluting the resultant paste with water, it is possible to prepare suspensions of any desired concentration.

Emulsifiable Concentrate

The following ingredients are mixed to formulate a 25% emulsifiable concentrate:
25 parts of a pyrimidine of the formula I,
5 parts of a mixture of nonylphenolpolyoxyethylene and calcium dodecylbenzenesulfonate,
15 parts of cyclohexanone,
55 parts of xylene.

This concentrate can be diluted with water to give emulsions in suitable concentrations of e.g. 0.1 to 10%. Such emulsions are suitable for controlling weeds in crops of cultivated plants.

EXAMPLE 6

The pre- and postemergence herbicidal activity of the compounds of the invention was determined by means of the following tests Preemergence herbicidal activity (germination inhibition)

In a greenhouse, directly after sowing the test plants, in seed dishes, the surface of the soil is treated with an aqueous dispersion of active ingredient obtained from a 25% emulsifiable concentrate or from a 25% wettable powder with active ingredients which, because of insufficient solubility, cannot be formulated to emulsifiable concentrates. Four different concentration series are used, corresponding to 4, 2, 1 and 0.5 kg of active ingredient per hectare. The seed dishes are kept in the greenhouse at 22°–25° C. and 50 to 70% relative humidity, and the test is evaluated after 3 weeks.

In this test, compounds 1, 2 and 3 are most effective against the broad-leafed and also most grass-like weeds, whilst cultivated plants such as maize, and also to some extent wheat, millet, rice, soybeans and cotton, are not damaged or suffer only minor damage.

Postemergence herbicidal activity (contact action)

A large number of weeds and cultivated plants (both monocots and dicots) are sprayed postemergence in the 4- to 6-leaf stage with an aqueous active ingredient dispersion at rates of application of 0.5, 1, 2, and 4 kg/ha, and then kept at 24°–26° C. and 45–60% relative humidity. The test is evaluated at least 15 days after treatment. In this test too, compounds 1, 2 and 3 are most effective against the broad-leafed and most grass-like weeds, whilst maize, barley, millet, rice, as well as cotton and soybeans are not damaged or are damaged only at higher rates of application.

Growth inhibition in grasses

Seeds of the grasses Lolium parenne, Poa pratensis, Festuca ovina, and Cynodon dactylon are sown in plastic dishes filled with an earth/turf/sand mixture (6:3:1) and watered as required. The emergent grasses are cut back weekly to a height of 4 cm above the soil and 50 days after sowing and, 1 day after the last cut, are sprayed with aqueous spray mixtures of an active ingredient of the formula I. The concentration of active ingredient corresponds to a rate of application of 0.5 and 2.5 kg per hectare. The growth of the grasses is evaluated 21 days after application.

Growth inhibition in cereals

Summer barley (Hordeum vulgare) and rye (Secale) are sown in sterilised soil in plastic beakers in a greenhouse and watered as required. The cereal shoots are treated 5 days after sowing with a spray mixture of a compound of the formula I. The rate of application corresponds to 0.5 and 2.5 kg of active ingredient per hectare. Evaluation of growth is made 10 and 21 days after application. Compounds 1, 2 and 3 effect pronounced growth inhibition both in cereals and in grasses.

In a further aspect, the present invention is also concerned with the production of 5-sulfinylpyrimidines and with these novel compounds themselves. They are used as intermediates for obtaining the pyrimidines of the formula I or also of dyes.

The 5-sulfinylpyrimidines have the formula IX

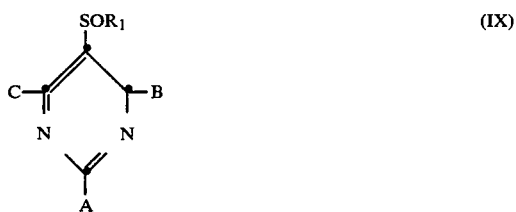

(IX)

wherein each of A, B and C is a chlorine, bromine or fluorine atom, or one of A, B and C is also an amino group —$NR_2R_3$, $R_1$ is $C_1$–$C_4$alkyl and each of $R_2$ and $R_3$ is hydrogen, $C_1$–$C_6$alkyl or $C_3$–$C_6$cycloalkyl.

The alkyl groups comprise all straight-chain and branched groups which contain the corresponding number of carbon atoms.

The 5-sulfinylpyrimidines are novel compounds. 5-Alkylthiopyrimidines of similar constitution are described in J. of Medicinal Chemistry 18, p. 553 (1975). The production of 5-alkylsulfonyl-trichloropyrimidine is described in French patent 2 390 436 and in German Offenlegungsschrift 2 819 837.

The 5-alkylsulfinyl-2,4,6-trihalo- or 2,4,6-aminodihalopyrimidines of the formula I are obtained by oxidising a 2-alkylthio-2,4,6-trihalopyrimidine or a 2-alkylthio-2,4,6-amino-dihalopyrimidine of the formula X

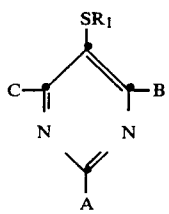

wherein A, B, C and $R_1$ have the given meanings, with a mild oxidising agent and, if desired, replacing a halogen atom A, B or C by the amino group $HNR_1R_2$.

The starting 2-alkylthio-2,4,6-trihalopyrimidines are described in J. of Medicinal Chemistry. Examples of mild oxidising agents are: peracetic acid, 3-chloroperbenzoic acid, perbenzoic acid, hydrogen peroxide, sodium periodate, perlauric acid, iodobenzodichloride, N-chlorosuccinimide, and N-bromosuccinimide. Depending on the oxidising agent employed, suitable solvents are methylene chloride, chloroform, acetic acid, water etc. The oxidisation is carried out in the temperature range from $-50°$ to $+50°$ C. Similar oxidation reactions are described e.g. in Tetrahedron Letters 1973, p. 2365, cf. also "Organic Compounds of Bivalent Sulfur", Vol. 2, p. 64 (Chemical Publishing C., New York).

Compounds of the formula IX, wherein A, B and C are bromine or fluorine atoms, can also be obtained by reacting compounds of the formula IX of this invention, wherein all three substituents A, B and C are chlorine atoms, with a brominating or fluorinating agent such as phosphorus tribromide, aqueous hydrogen fluorine, an alkali metal fluoride or potassium fluorosulfinate, until one, two or all three chlorine atoms are replaced by bromine or fluorine atoms.

Thus e.g. the compounds of the formula IX, wherein A, B and C are chlorine and $SR_1$ has the given meaning, can be converted to the bromine or fluorine analogues, by converting 5-alkylsulfinyl-2,4,6-trichloropyrimidine, e.g. 5-methylsulfinyl-2,4,6-trichloropyrimidine, with phosphorus tribromide, which can also act as solvent, to the corresponding 2,4,6-tribromopyrimidine, or by converting the 2,4,6-trichloro compound by reaction with aqueous hydrogen fluoride, potassium fluorosulfinate or an alkali metal fluoride, undiluted or in the presence of a high-boiling aprotic organic solvent, to the corresponding 2,4,6-trifluoro compound. Suitable solvents for this transhalogenation are e.g. aromatic hydrocarbons such as toluene, benzene and xylene; N,N-dialkylamides of aliphatic monocarboxylic acids of the above mentioned kind, such as N,N-dimethyl formamide and N,N-dimethyl acetamide; dialkyl sulfoxides, especially dimethyl sulfoxide; cyclic ethers and cyclic amides such as tetrahydrofurane, tetrahydropropane, N-methyl-2-pyrrolidone and N-acetyl-2-pyrrolidone; hexamethylphosphoric triamide (hexametapol); N,N,N',N'-tetramethylurea, and tetrahydrothiophene dioxide (sulfolane).

The reaction temperature for the transhalogenation is advantageously in the range from 20° to 250° C., with the preferred range being from 50° to 130° C.

The production of the 5-sulfinylpyrimidines of the formula IX is described in Example 4a. Further 5-sulfinylpyrimidines which are obtained by analogous procedures are listed in the following table.

| $SOR_1$ | A | B | C | Physical data (°C.) |
|---|---|---|---|---|
| $SOCH_3$ | Cl | Cl | Cl | m.p. 126–8° |
| $SOCH_3$ | $NH_2$ | Br | Br | |
| $SOCH_3$ | $NH_2$ | Cl | Cl | m.p. 215–6° |
| $SOC_2H_5$ | Cl | Cl | Cl | |
| $SOC_4H_9$ | Cl | Cl | Cl | |
| $SOC_4H_7n$ | Cl | Cl | Cl | |
| $SOC_3H_7iso$ | Cl | Cl | Cl | |
| $SOC_4H_9tert.$ | Cl | Cl | Cl | |
| $SOCH_3$ | F | F | F | m.p. 46–48° |
| $SOCH_3$ | Br | Br | Br | |

What is claimed is:

1. A pyrimidine of the formula I

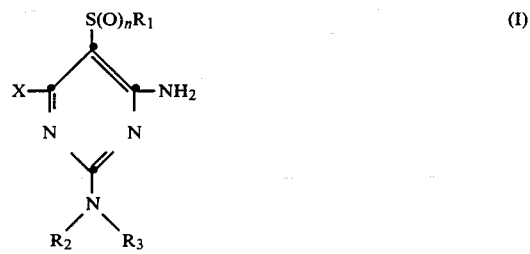

wherein n is 1 or 2, $R_1$ is $C_1$–$C_4$alkyl, each of $R_2$ and $R_3$ is hydrogen, $C_1$–$C_6$alkyl or $C_3$–$C_6$cycloalkyl, and X is chlorine, bromine or fluorine.

2. 4-Amino-2-methylamino-5-methylsulfonyl-6-chloropyrimidine according to claim 1.

3. 2,4-Diamino-5-methylsulfonyl-6-chloropyrimidine according to claim 1.

4. 2-Methylamino-4-amino-5-methylsulfinyl-6-chloropyrimidine according to claim 1.

5. A herbicidal and plant growth-regulating composition which contains, as active ingredient, an effective amount of a and a carrier pyrimidine of the formula I in claim 1.

6. A method of selectively controlling weeds in a crop of useful plants, which comprises applying to said crop a herbicidally effective amount of a pyrimidine of the formula I according to claim 1, or of a composition containing such a compound.

7. A method according to claim 6, wherein the crop is a maize crop.

8. A method of inhibiting growth in crops of cereals which comprises applying thereto a growth promoting effective amount of a pyrimidine of the formula I according to claim 1.

9. A pyrimidine having the formula

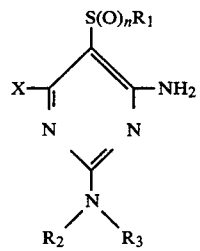

wherein
n is 1 or 2,
$R_1$ is $C_1$–$C_4$ alkyl,
each of $R_2$ and $R_3$ is hydrogen or $C_1$–$C_6$alkyl, and
X is chlorine, bromine or fluorine.

* * * * *